United States Patent [19]

Heusquin et al.

[11] Patent Number: 4,878,043
[45] Date of Patent: Oct. 31, 1989

[54] DEVICE FOR INDICATING HYDROCULTURE-RELATED VALUES

[76] Inventors: Guy Heusquin; Anke Heusquin, both of 19 Rodgy Thier, B-4500 Liège-Jupille, Belgium

[21] Appl. No.: 120,974
[22] Filed: Nov. 16, 1987

[30] Foreign Application Priority Data

Nov. 20, 1986 [DE] Fed. Rep. of Germany ....... 3639695

[51] Int. Cl.⁴ ..................... G08B 19/00; G08B 21/00
[52] U.S. Cl. ..................... 340/521; 340/596; 340/602; 340/604; 340/620; 324/61 P; 324/65 P; 200/190
[58] Field of Search ............... 340/521, 592, 595–599, 340/602–604, 618, 620; 324/61 R, 61 P, 65 R, 65 P; 73/338, 73, 335, 336.5; 200/182, 190

[56] References Cited

U.S. PATENT DOCUMENTS

| | | | |
|---|---|---|---|
| 3,882,383 | 5/1975 | Matlin ........................... | 340/604 |
| 3,927,370 | 12/1975 | De Bough ........................ | 340/604 |
| 4,020,417 | 4/1977 | Brehob et al. ................... | 340/602 |
| 4,122,389 | 10/1978 | Haagen .......................... | 340/604 |
| 4,268,824 | 5/1981 | Phillips ........................ | 340/604 |
| 4,319,485 | 3/1982 | Terada et al. ................... | 340/602 |
| 4,514,722 | 4/1985 | Batcheler et al. ................ | 340/604 |

Primary Examiner—Donnie L. Crosland
Attorney, Agent, or Firm—Walter A. Hackler

[57] ABSTRACT

A device for indicating values which are of interest in hydroculture applications is characterized in that the device includes a tube open at one end thereof and attached to a vessel at another end thereof. A probe including a sensor is disposed proximate the one end of the tube for responding to liquid. An IC connected to the sensor includes an electronic system 12 and an optical or acoustic signal transmitter (15) is connected to the electronic system galvanically or in a wireless manner. This arrangement makes it possible to reliably indicate any absence of liquid and to read the indication with ease.

16 Claims, 2 Drawing Sheets

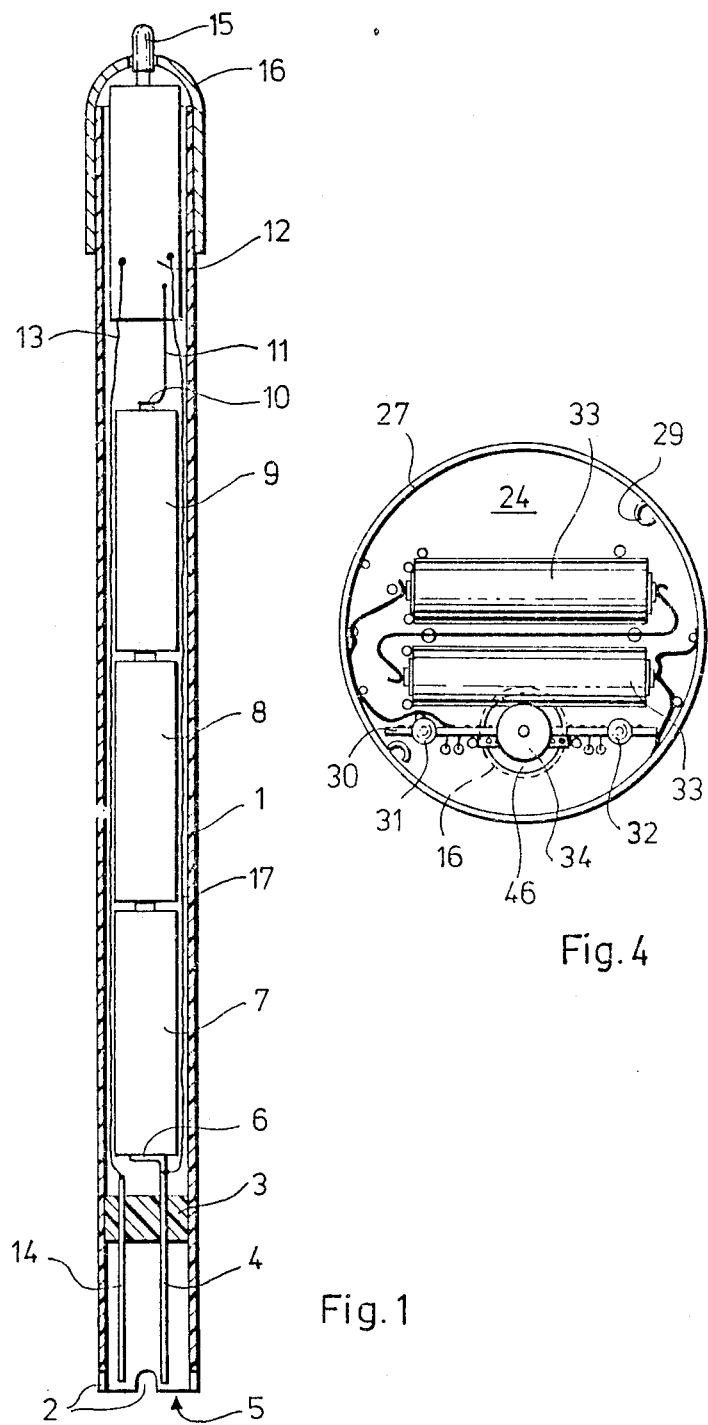

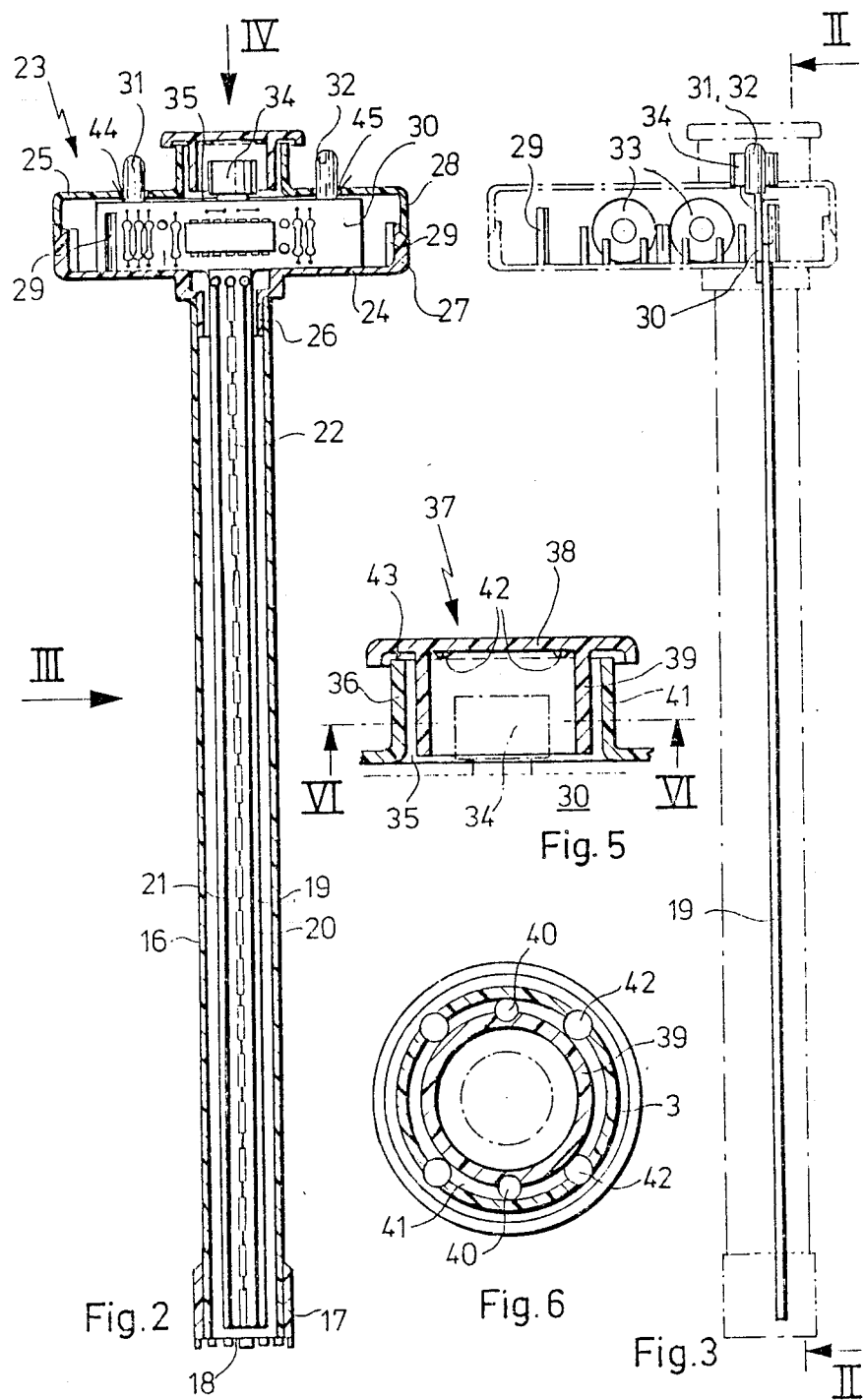

DEVICE FOR INDICATING HYDROCULTURE-RELATED VALUES

The present invention relates to a device for indicating measured values encountered in hydroculture applications in and/or near a container suited for growing plants and containing porous bodies suited for carrying out the hydroculture process.

Known devices of this type are tubular in shape, open at their lower ends and equipped with a float which is raised by the liquid in the container so that the vertical position of the float provides the desired information on the level of nutrient solution present in the container.

These known devices function only as water-level indicators. They provide a "no water" indication already when a certain residual quantity of liquid is still present in the container. This is undesirable because the plants develop best when the porous bodies absorbing the nutrient solution are permitted to get dry periodically. In addition, these waterlevel indicators tend to get dirty in which case it is often no longer possible to read exactly the indication provided by the float.

Now, it is the object of the present invention to eliminate the described disadvantages and to provide a device which indicates reliably the absence of liquid in the container, which is easy to handle and provides an easily readable indication.

This object is achieved according to the invention by an arrangement in which the device is provided at its lower end with a sensor responding to liquid, an IC connected to the said sensor and comprising an electronic circuit (electronic system 12) and an optical or acoustic signal transmitter (15) connected to the said electronic system galvanically or in a wireless manner.

The present invention provides the advantage that when the housing of the device extends right down to the bottom of the container, the sensor will respond only when actually no residual liquid is left in the container and that the electronic unit permits the indication to be transmitted to any desired point where easy reading thereof is possible. According to one embodiment of the invention, the indication can be read at a portion of the housing projecting upwardly from the container or from the porous bodies filled into the container, or else at a point remote from the device and the container. Another advantage of the present invention is provided by the use of the electronic system which, when selected appropriately, is capable not only of providing a corresponding signal indicating the presence or absence of liquid in the container, but also of performing additional functions and of converting the information obtained into corresponding signals for transmission to suitable indication devices.

According to certain embodiments of the invention, the sensor may comprise two electrodes arranged at the lower end of the housing, which said electrodes may also consist of a conductive portion of the housing on the one hand and an electrode insulated from this portion on the other hand. An electrode arrangement of this type is very robust and easy to produce. It is suited for use not only in connection with embodiments of the invention where the electronic unit provides a signal when the electric resistance between the electrodes corresponds to the absence of liquid in the container, i.e. when the resistance assumes extremely high values. Rather, an electrode arrangement of this type can be used in other embodiments of the invention also for causing the electronic system to emit a signal when an adjustable resistance value corresponding to a specific pH value of the liquid prevails between the electrodes so that in this case the device comprises a sensor for the pH value of the liquid. However, a sensor for the pH value may also have a design different from the one described before, comprising two physically separate electrodes, and may for example comprise a so-called alkali electrode. According to certain embodiments of the invention, the sensor for the pH value may be connected to a device displaying continuously the pH value, and when two electrodes are used as sensor for the pH value, the electrodes may be connected to a device indicating the electric resistance prevailing between the electrodes so that the pH value can be read directly on the scale of the device.

The device may be attached to or installed in the container wall or may be designed as a separate unit for being introduced into the container in the same manner as the known devices which serve the only function to indicate the water level by means of a float.

In the case of the embodiment described last, the device may have the known, substantially tubular shape, with the sensor responding to liquid being arranged at its lower end. However, an additional sensor responding to liquid is arranged at a certain distance from the lower end of the device for providing a signal, for example to a buzzer or the like, when the liquid level has reached the level of the sensor. This permits a specific liquid level to be observed when filling liquid, for example a nutrient solution, into the container.

According to certain embodiments of the invention, the device may comprise a thermometer for the temperature of the liquid in the container and/or the temperature prevailing around the container. The thermometer reading may be provided either directly at the device, or else the thermometer may supply signals to the electronic system for transmission to an indicating device, for example a recording indicating device or one which supplies an optical or acoustic signal when a specific temperature is reached.

This embodiment of the invention may be implemented in such a manner that the electronic system comprises a connection for the control line of a heating which can be controlled by signals supplied from the electronic system. This permits to control both the temperature of the liquid in the container and the temperature around the plants.

According to certain embodiments of the invention, the device may be powered by batteries or other energy sources. Preferably, the batteries required for powering the installations contained in the device are accommodated in the device itself. For charging the batteries, solar cells may be provided.

According to certain other embodiments of the invention, one end of the device, which projects from the content of the container comprising the porous balls, may be provided with a small lamp connected to the electronic unit for providing, for example, flashing signals when no liquid is left in the container. Instead of the lamp, a buzzer may also be provided, the signal transmitters being controlled directly by the electronic system.

Other embodiments of the invention comprise a light-sensitive sensor and a device indicating the averaged value of the quantity of light measured, for example, during the past 12 or 24 hours. It is possible in this manner to see if the luminous conditions are optimally suited for the respective plant or if, for example, the plant should be exposed to the radiation of an additional lamp. It goes without saying that such a lamp may be switched on also in a controlled manner by the electronic unit when the measured quantity of light, averaged over a certain period of time, is short of a given value.

Although the device of the invention may itself be provided with the indicating means, the devices for indicating the values determined by the device may, alternatively, also be arranged at a point remote from the device in which case the indicating devices may be connected to the device either via electric conductors or in a wireless manner. The device may be used with particular advantage in hydroculture installations comprising a great number of plant containers in which case the device may either be installed directly in the container or else exhibit a tubular shape and be inserted loosely into the container. Preferably, the measured values are then transmitted to an indicator board where the values are displayed, related to the individual containers, so that information is always provided as to which container of the hydroculture or which flower stand is requiring care at any moment. If the hydroculture installation comprises a plurality of containers, the device itself may comprise only the sensors for the values to be measured and transmission means for transmitting the measured values to a central electronic processing unit, for further processing.

According to one embodiment of the invention, the device comprises a tube extending downwardly and carrying at its upper end a vessel whose central plane extends at a right angle to the tube axis. This device may, conveniently, be designed in such a manner that the batteries and/or the electronic unit and/or the signal transmitter are arranged in the vessel. This feature provides the advantage that the downwardly extending tube, which comprises the probe, may have a relatively small diameter since there is no necessity to accommodate the batteries in the tube. In addition, this embodiment provides the advantage that no parts essential for the operation of the device, for example batteries or the like, which are sensitive to humidity, will be affected in the event the tube should fill with water due to an excessive supply of water or to untightness.

The tube may include a probe which may extend right to its lower end and which may, for example, consist of a fiber glass material and carry the electric conductors leading to the sensor. Conveniently, the tube may be connected to the vessel eccentrically so that when the tube is arranged near one edge of the container used for hydroculture, the flat vessel extends either as far as possible or, in another position, as little as possible, or not at all, beyond the edge of the container.

According to one further improvement of the embodiment of the invention comprising a vessel arranged at the upper end of the tube, the electronic system may be arranged on a strip mounted detachably in the said vessel. The strip may also carry the probe which, accordingly, can be removed from the vessel together with the strip carrying the electronic system. According to one embodiment of the invention, the flat vessel is fitted detachably on the tube and the lower portion of the tube is provided with recesses. This permits low-cost production of both the tube and the vessel.

According to another further improvement of the embodiment of the invention comprising a vessel arranged at the upper end of the tube, the vessel consists of a dish-shaped bottom part and a dish-shaped lid; accordingly, the bottom and the lid may be provided each with a marginal strip projecting from the bottom and the lid in the form of a rim. The bottom portion and the lid are fitted to each other by means of these marginal strips and are retained in position relative to each other by static friction; or else the marginal strips of the bottom and the lid may be additionally connected in a form-locking manner. As a further alternative, the bottom and the lid may be connected by suitable detent means. According to certain embodiments of the invention, the vessel may be flat and of circular shape.

According to certain embodiments of the invention, the lid of the vessel may be provided with openings accommodating luminous diodes which indicate the condition regarding the interesting values. For example, a green diode may be used to indicate that the water in the hydroculture container exhibits the desired level, while a red luminous diode may light up when the water level in the container is either above or below the desired level. The luminous diodes may, conveniently, be mounted on the strip carrying the electronic system which renders the assembly, and any repairs, of the device extremely easy since the optical signal transmitters are not mounted on the lid.

According to one embodiment of the invention, the lid is provided with an opening, and the acoustic signal transmitter projects upwardly through this opening. This arrangement provides the advantage to make the acoustic signal much more audible than when the signal transmitter is accommodated inside the vessel, sealed off from the outside. The opening through which the signal transmitter projects upwardly may be sealed off by a hood which then comprises openings as passages for the switch. In order to ensure that no water will be allowed to enter the vessel, even if the plants are watered carelessly, the hood covering up the openings in the lid is provided with channels which are in turn covered up on top by a cover which prevents any water from entering these channels, though being arranged at a distance from the upper ends of the channels large enough to ensure that the sound emitted through the upper ends of the channels can spread properly. Such a hood may, according to certain embodiments of the invention, consist of a tubular portion which is mounted on the upper edge of the opening and which can be closed by a plug in such a manner that the plug extends beyond the upper edge of the tubular portion, at a certain distance therefrom, so as to provide sound communication between the interior of the vessel and the outside.

Other features of the invention will become apparent from the following description of one embodiment of the invention when read with reference to the claims and the drawing. The individual features of the invention may be incorporated in embodiments of the invention either individually or in any desired combination thereof.

Certain embodiments of the invention are represented in the drawing in which

FIG. 1 shows a longitudinal section through one embodiment of the invention;

FIG. 2 shows a longitudinal section through another embodiment of the invention;

FIG. 3 is a view in the direction of arrow III in FIG. 2 showing the interior of the vessel, with the walls of the vessel broken away and a probe mounted on a strip, without the tube;

FIG. 4 shows a top view of the vessel, without lid;

FIG. 5 shows an enlarged representation of a hood-like cover for an opening in the lid of the vessel; and, FIG. 6 shows a section along line VI—VI in FIG. 5.

The embodiment of the invention represented in FIG. 1 comprises a tubular housing 1 made of a plastic material, for example a PVC material, which may have a length of approx. 25 cm and a diameter of approx. 2 cm. The lower, open end of the housing 1 is provided with recesses 2 cut into the lower edge of the housing wall. Spaced from the lower end, for example by approx. 2 cm, there is provided a seal 3 which may consist of a plug made from an elastic expanded foam, for example a silicon-based plastic material. This seal 3 is passed by an electrode 4 ending at a distance of approx. 2 mm from the plane of the lower edge 5 of the housing 1. The upper end of the electrode 4 is bent off approximately at a right angle so that the bent-off portion 6 exhibits the shape of a leaf and resilient properties. The upper portion 6 of the electrode 4 supports a cylindrical cell 7 followed by a cylindrical cell 8 which is in turn followed by another cylindrical cell 9. The three batteries 7, 8 and 9 are connected in series. The upper end (positive pole) of the cylindrical cell 9 is in contact with the lower end 10 of an electrode 11 mounted on a circuit board 12. The circuit board 12 comprises integrated circuits (IC) of an electronic circuit which will be described hereafter shortly as "electronic system" the latter being designed in a suitable manner to perform all the functions required to achieve the effects described above. A line 13 leads from the electronic system 12 to an electrode 14 which is likewise mounted in the sealing plug 3 and whose lower end also extends almost to the plane formed by the lower edge 5 of the housing. The electrodes 4 and 14 form together a fluid-sensitive sensor. When the two electrodes 4 and 14 are immersed in an aqueous liquid, for example the nutrient solution used in hydroculture, a relatively low resistance will be obtained between the two electrodes 4 and 14. In the absence of any liquid, however, the resistance between the two electrodes 4 and 14 is extremely high. In this case, the electronic system 12 supplies signals to a lamp 15 mounted in a cap 16 fixed at the upper end of the tubular housing 1, thereby causing the lamp 15 to start flashing intermittently.

The entire device is inserted into a container accommodating the porous bodies generally used in hydroculture applications, together with the plant growing therein and the nutrient solution. The device is introduced into the container until its lower edge 5 comes to rest on the bottom of the container. If no nutrient solution is present in the container, there is also no liquid between the electrodes 4 and 14 so that the resistance between these electrodes rises to a very high value and the lamp 15 starts flashing intermittently. According to certain embodiments of the invention, the electrodes 4 and 14 may also extend right into the plane of the lower edge 5, or even some fractions of a mm beyond the latter. The nearer the lower ends of the electrodes 4 and 14 get to the bottom of the container, the smaller is the amount of residual liquid left in the container when the lamp 15 starts emitting the optical signal reminding the user that new nutrient solution has to be filled in.

The negative pole of the battery is connected to the electronic system 12 via a line 17.

The device can be manufactured in different sizes and heights, its upper end may be approximatively at the same level as the border of the container when the lower end of the device rests on the bottom of the container which contains the hydroculture.

Other embodiments of the devices implementing the before-described features may be designed also for use in aquariums.

There may be provided a circuit for suppressing the acoustic signal during the night.

The device may be employed also in connection with plants cultivated in earth.

In the case of the embodiment of the invention represented in FIGS. 2 to 6, a tube 16 corresponding to the tube 1 comprises at its lower end a sleeve 17 mounted on the lower end of the tube and provided with recesses 18 on its face which serve as passages for the liquid. Inside the tube 16, there is provided a flat rod 19 consisting of a fiber glass material and carrying on its surface two electric conductors 20 and 21. A third conductor 22 arranged between the said conductors 20 and 21, at a certain distance therefrom, consists of alternating sections of smaller and greater cross-section. By scraping off a thin section it is possible to interrupt this conductor at any desired height, for example at the height of the desired water level. The conductors may be applied on the rod by the usual metal-coating techniques. In order to prevent corrosion, they may consist of a tin and copper alloy, or of gold-plated copper or even of platinum, either over the whole length of only in the area of their lower ends.

Fitted to the upper end of the tube 16 is a flat vessel 23 consisting of a bottom 24 and a lid 25. The bottom 24 comprises a downwardly directed connection piece 26, arranged at the edge of a recess 46, by which the vessel 23 is fitted in and fixed to the upper end of the tube 16, leaving suitable vent slots. The bottom 24 is further provided with a rim 27 projecting upwardly in the form of a wall, while the lid 25 is provided on its edge with a downwardly directed marginal strip 28, the bottom 24 and the lid 25 of the flat, generally circular vessel being fitted together by the free edges of the rim 27 and strip 28, respectively, and retained in position relative to each other by static friction. To provide improved retention, the bottom part 24 may be provided with additional locking pins 29 with barbs provided at their upper ends for engaging the receiving element (not shown in the drawing) in the lid 25.

The vessel 23 accommodates in its interior a strip 30 carrying the switching elements of the electronic system and two luminous diodes 31 and 32. Further, the rod 19 is fixed to the said strip 30. In addition, the vessel is designed to accommodate two batteries 33 serving as power source and an acoustic signal transmitter 34 is mounted on the strip 30 to project upwardly through an opening 35 in the lid 25. A tubular portion 36 formed integrally with the lid, at the edge of the opening 35, is closed by a plug 37 surrounding the acoustic signal transmitter 34 at a certain distance. The plug 37 consists of a lid portion 38 with a tubular portion 39 formed integrally therewith and having an outer diameter somewhat smaller than the inner diameter of the tubular portion 36 so that an annular channel 41, which is subdivided by spacers 40 and which opens into the interior of the vessel 23, is formed between the tubular portion 36 and the tubular portion 39. When the plug 37 is pushed into the tubular portion 36, spacers 42, which are formed integrally with the inner surface of the lid 38, come to rest upon the upper end face 43 of the tubular portion 36 so as to maintain a certain distance between the inner surface of the lid 38 and the annular end face 43. Accordingly, the sound produced by the signal transmitter can escape to the outside through the channel 41 and the space between the inner surface of the lid 38 and the annular end face 43. The lid 38 extends a certain distance beyond the annular end face 43 so as to cover up the channel 41 to prevent any water from entering the channel 41 during watering of the plants.

Two small openings 44 and 45 provided in the lid 25 serve as passages for the luminous diodes 31 and 32.

The strip 30 is mounted detachably inside the vessel 23. The tube 16 is mounted on the vessel 23 in an eccentric position.

The index of pH may be determined by measuring the electrical resistance or by measuring the concentration of particular ions by means of an electrode responsive to the ions (glass electrode) or by a color reaction with a particular reagent. In the last mentioned case the device may comprise a small pump (suction bulb made from rubber or the like) for taking a small quantity of liquid and a receptacle into which the quantity of liquid is introduced and into which a predetermined amount of a reagent or for example a strip of paper impregnated with a reagent is introduced.

We claim:

1. A device for indicating values which are of interest in hydroculture applications comprising:
   a tube open at one end thereof and attached to a vessel at another end thereof;
   probe means, comprising at least one sensor and disposed proximate said tube one end, for responding to a liquid;
   an IC connected to said sensor and comprising an electronic system;
   strip means for supporting said probe means and said electronic system; and
   means for removably mounting said strip means, within said tube and vessel in order to facilitate removal of said probe and electronic system for maintenance while said tube and vessel remain insitu in a hydroculture medium 2. The device according to claim 1, wherein said sensor comprises two electrodes.

3. The device according to claim 1 or 2, wherein said electronic system provides a signal when the electrical resistance between the electrodes corresponds to the absence of liquid in the hydroculture medium.

4. The device according to claim 3 wherein said electronic system is configured for emitting a signal when an adjustable resistance value is reached between the electrodes.

5. The device according to claim 4 further comprising means for indicating the resistance value between the electrodes with a scale displaying pH valves corresponding to respective resistance valves.

6. The device according to claim 1 further comprising additional sensor means for responding to the liquid, said additional sensor means being disposed at a certain distance from the tube one end.

7. The device according to claim 6 further comprising a buzzer controlled by said additional sensor means.

8. The device according to claim 1 further comprising a thermometer interconnected with said electronic system.

9. The device according to claim 8 wherein said thermometer is connected to said electronic system and the latter emits signals in response to the temperature.

10. The device according to claim 9 wherein said electronic system comprises means for controlling a heater.

11. The device according to claim 1 further comprising batteries for supplying power to the electronic system in the device.

12. The device according to claim 11 further comprising solar cell means for charging the batteries.

13. The device according to claim 1 further comprising a light-sensitive sensor interconnected with means for indicating the averaged value of the quantity of light measured for a period of time.

14. The device according to claim 1 further comprises means for releasably attaching said vessel and tube to one another.

15. The device according to claim 1 further comprising means for attaching said device to the wall of a container.

16. The device according to claim 1 further comprising means for installing said device in the wall of a container.

* * * * *